US00PP33786P2

(12) United States Plant Patent
Trees

(10) Patent No.: US PP33,786 P2
(45) Date of Patent: Dec. 28, 2021

(54) ***SPIRAEA* PLANT NAMED 'ICECONSPIR'**

(50) Latin Name: *Spiraea japonica*
Varietal Denomination: Iceconspir

(71) Applicant: THE CONARD PYLE COMPANY, West Grove, PA (US)

(72) Inventor: Scott C. Trees, Arroyo Grande, CA (US)

(73) Assignee: THE CONARD PYLE COMPANY, West Grove, PA (US)

( * ) Notice: Subject to any disclaimer, the term of this patent is extended or adjusted under 35 U.S.C. 154(b) by 0 days.

(21) Appl. No.: 17/130,998

(22) Filed: Dec. 22, 2020

(51) Int. Cl.
*A01H 5/02* (2018.01)
*A01H 6/74* (2018.01)

(52) U.S. Cl.
USPC ..... Plt./226
CPC ..... *A01H 6/74* (2018.05)

(58) Field of Classification Search
USPC ..... Plt./226
CPC ..... A01H 6/74
See application file for complete search history.

(56) References Cited

U.S. PATENT DOCUMENTS

PP26,995 P3 8/2016 Wood

*Primary Examiner* — Keith O. Robinson
(74) *Attorney, Agent, or Firm* — Panitch Schwarze Belisario & Nadel LLP; Stephany G. Small; Travis W. Bliss

(57) ABSTRACT

A new and distinct variety of *Spiraea* plant, referred to by its cultivar name, 'Iceconspir', is disclosed. The new variety forms attractive pink colored flowers. Attractive, blue-green colored foliage with burgundy colored new growth is formed. The growth habit is compact, mounded. The new variety is well suited for providing attractive ornamentation in the landscape.

2 Drawing Sheets

Botanical/commercial classification:
Latin name: *Spiraea japonica.*
Varietal denomination: 'Iceconspir'.

SUMMARY OF THE INVENTION

The new variety of *Spiraea japonica* plant originated in a controlled breeding program in Guadalupe, Calif. during June 2014. The objective of the breeding program was the development of a series of *Spiraea* cultivars having distinguishing foliage and flowers. The new cultivar was created by cross-pollination wherein two parents were crossed which previously had been studied in the hope that they would contribute the desired characteristics. The female parent (i.e., the seed parent) was the 'Crispa' variety (non-patented). The male parent (i.e, the pollen parent) was the 'Norman' variety (non-patented).

The parentage of the new variety can be summarized as follows:

'Crispa' x 'Norman'

The new cultivar was discovered and selected as a single flowering plant from the progeny resulting from the above stated cross-pollination during May 2015 in a controlled environment in Guadalupe, Calif. Selective study resulted in the identification of a single plant of the new variety.

It was found that the new variety of *Spiraea* plant of the present invention:

(a) forms pink colored flowers,
(b) displays blue-green colored foliage with burgundy colored new growth, and
(c) forms a compact, mounding growth habit.

The new variety well meets the needs of the horticultural industry. It can be grown to advantage as ornamentation in parks, gardens, public areas, and in residential settings. Accordingly, the plant is particularly well suited for growing in the landscape.

The new variety of the present invention can readily be distinguished from its ancestors. More specifically, the 'Crispa' variety (i.e., the seed parent) displays deep pink colored flowers and dark green colored foliage, whereas the new variety provides pink colored flowers and blue-green colored foliage with burgundy colored new growth. The 'Norman' variety (i.e., the pollen parent) displays deep pink colored flowers and light green colored foliage, whereas the new variety displays pink colored flowers and blue-green colored foliage with burgundy colored new growth. Moreover, the new variety can also be distinguished from other similar varieties that are commercially available. For instance, the new variety of the present invention can readily be distinguished from the 'SMNSJMFP' variety (U.S. Plant Pat. No. 26,995), as the new cultivar displays a smaller foliage size compared to the 'SMNSJMFP' variety.

The new variety has been found to undergo asexual propagation by terminal stem cuttings. Asexual propagation by terminal stem cuttings in Guadalupe, Calif. since July 2015 has shown that the characteristics of the new variety are stable and are strictly transmissible by such asexual propagation from one generation to another. Accordingly, the new variety undergoes asexual propagation in a true-to-type manner.

The new variety has been named 'Iceconspir'.

The new variety was first offered for sale on Jan. 8, 2020 at Baltimore, Md. by the inventor or by another who obtained the new variety directly or indirectly from the inventor.

BRIEF DESCRIPTION OF THE PHOTOGRAPHS

The accompanying photographs show as nearly true as it is reasonably possible to make the same, in a color illustration of this character, typical specimens of the plant and plant parts of the new variety. Colors in the photographs may differ slightly from the color values cited in the detailed description, which accurately describes the colors of the 'Iceconspir' variety. The plants were approximately 4 months of age and grown outdoors in one-gallon containers in Cochranville, Pa.

DETAILED BOTANICAL DESCRIPTION

Figure 1:
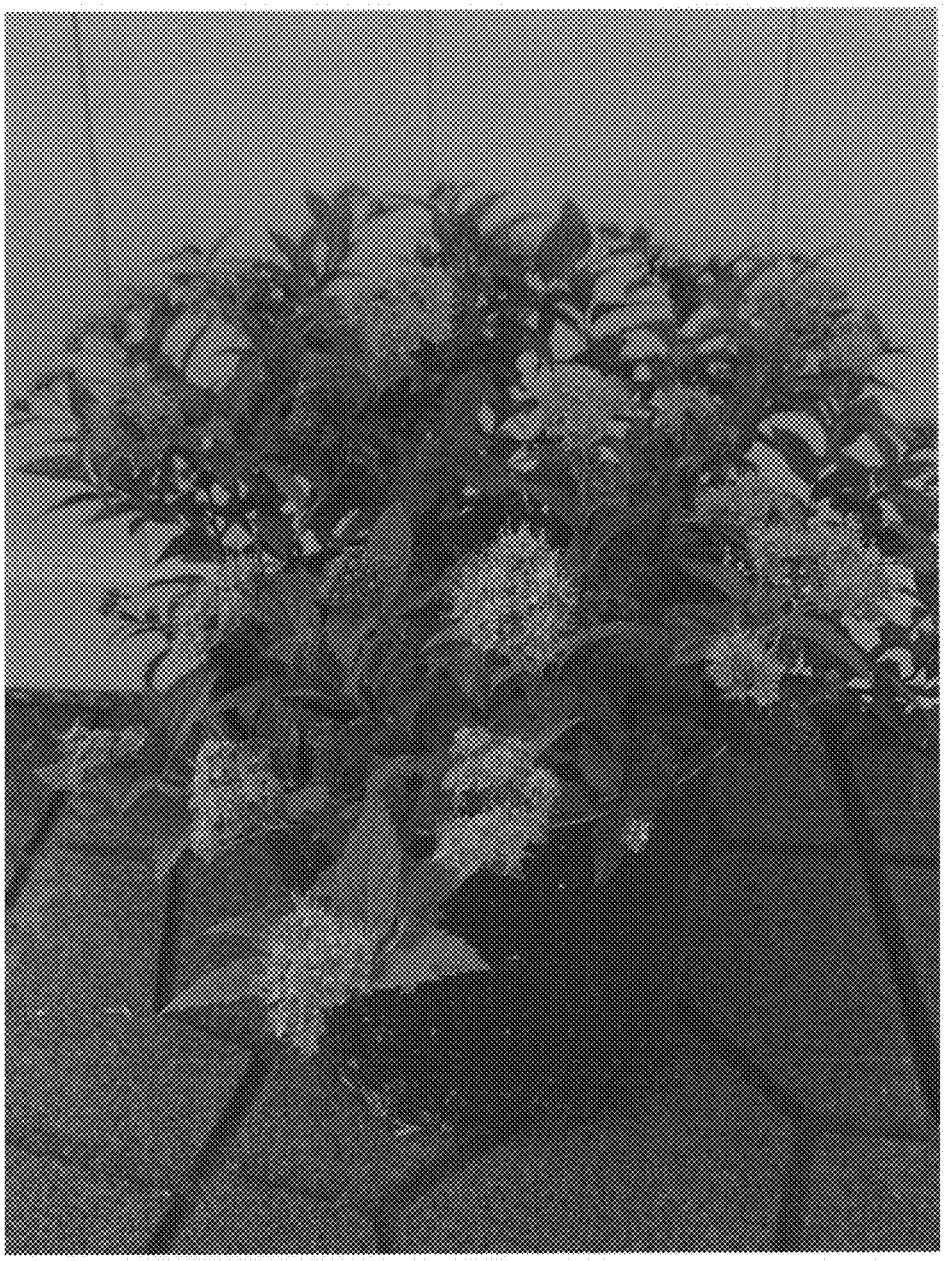
FIG. 1 illustrates a specimen of the plant displaying the overall growth and flowering habit—side view.
Figure 2:
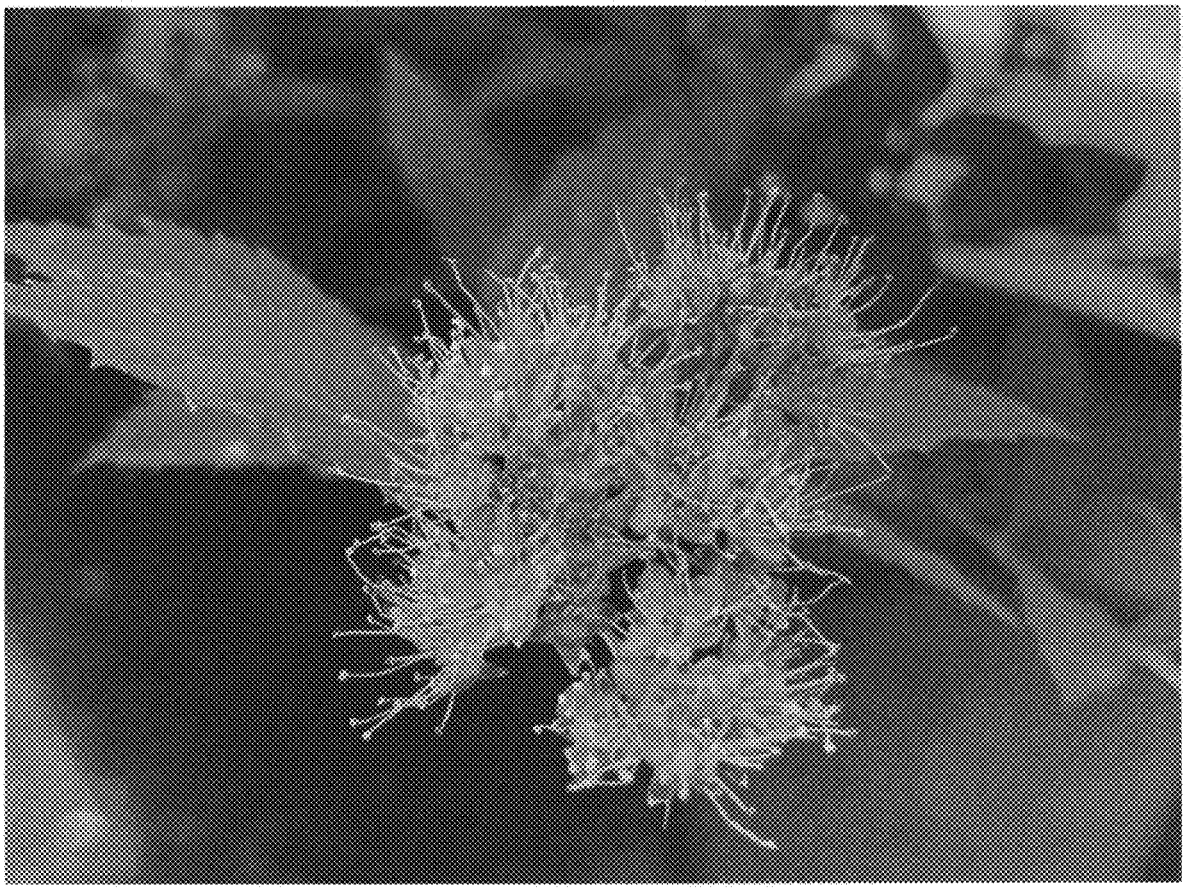
FIG. 2 illustrates a specimen of a flower cluster in the course of opening.

The chart used in the identification of the colors is that of The Royal Horticultural Society (R.H.S. Color Chart), 2015 edition, London, England. The terminology which precedes reference to the chart has been added to indicate the corresponding color in more common terms. The color values were determined in September 2020 under natural light conditions in Cochranville, Pa. The description is based on the observation of approximately four months old plants grown outdoors in one-gallon containers under conditions comparable to those used in commercial nursery practices in Cochranville, Pa.

Propagation:

*Type cutting.*—Terminal cuttings.

*Time to initiate roots.*—Approximately 14 days on average.

*Time to produce a rooted cutting.*—Approximately 48 days on average.

*Root description.*—Fibrous and fine; white to brown in color commonly between Greyed-Orange Group 163B and 165B.

*Rooting habit.*—Freely branching; dense,

Plant:

*Habit.*—Moderate vigorous, compact, low-mounding growth habit.

*Commercial crop time.*—Approximately 15 weeks from a rooted cutting to finish in a 19.0 cm container on average.

*Size.*—Approximately 19.0 cm in height from soil level to top of plant plane on average; approximately 30.0 cm in width on average.

Branches:

*Branching habit.*—Freely branching, pinching not required.

*Aspect.*—Erect to 45° from center.

*Lateral branch.*—Length: approximately 15.0 cm. Width: approximately 1.5 to 2.0 mm.

*Internode length.*—Approximately 1.0 cm.

*Color.*—Commonly near Grey-Brown Group N199C.

Foliage:

*Fragrance.*—None detected.

*Form.*—Simple.

Leaves:

*Aspect.*—45°.

*Type.*—Rhomboidal.

*Arrangement.*—Alternate.

*Shape.*—General: ovate. Margin: serrate. Apex: acute. Base: cuneate.

*Venation pattern.*—Pinnate.

*Size.*—Length of mature leaf: approximately 3.5 cm on average. Width of mature leaf: approximately 1.8 cm on average.

*Texture.*—Upper surface: glabrous, moderately rugose. Lower surface: glabrous, ribbed.

*Color.*—Upper surface of young foliage: commonly between near Greyed-Purple Group N186A with indistinguishable venation. Lower surface of young foliage: commonly a blend of near Greyed-Purple Group N187A and near Greyed-Purple Group 189A, with venation of near Greyed-Purple Group N187B. Upper surface of mature foliage: commonly near Green Group NN137A with indistinguishable venation. Lower surface of mature foliage: commonly near Green Group N138B with venation of near Green Group N138C.

*Leaf attachment.*—Petiolate.

*Petiole.*—Length: approximately 5.0 mm on average. Diameter: approximately 1.0 mm on average. Texture: smooth. Color: commonly near Greyed-Orange Group 166B.

Inflorescence:

*General description.*—Compound corymbs.

*Height.*—Approximately 2.0 cm on average.

*Diameter.*—Approximately 5.0 cm on average.

*Aspect.*—Facing upward to slightly outward.

*Fragrance.*—Slightly sweet.

*Number of flowers per inflorescence.*—Up to 100 on average.

Flower:

*Type.*—Single, rotate, not persistent.

*Aspect.*—Upright.

*Bud just before opening.*—Shape: globose. Length: approximately 4.0 mm on average. Diameter: approximately 2.0 mm on average. Color of petals: commonly between near Red-Purple Group 70A and near Red-Purple Group 70B.

*Corolla.*—Diameter: approximately 7.0 mm on average. Depth: approximately 3.0 cm on average.

*Petals.*—Quantity: 5, in a single whorl. Shape: orbicular. Margin: entire. Apex: rounded. Base: obtuse. Length: approximately 2.0 mm on average. Width: approximately 2.0 mm on average. Texture of upper and lower surfaces: glabrous. Color of upper and lower surfaces when first and fully open: commonly between near Red-Purple Group 70B and near Red-Purple Group 70C.

*Calyx.*—Shape: rounded. Length: approximately 2.0 mm on average. Diameter: approximately 4.0 mm on average.

*Sepal.*—Arrangement: fused in a circle around the petiole. Texture: smooth. Shape: round. Margin: entire. Apex: five distinct apices that are acute in shape. Base: fused. Length: approximately 1.0 mm for each segment. Width: approximately 2.0 mm for each segment. Color: commonly near Green Group 138B. Number: 5 sepals fused together at the base.

*Peduncle.*—Length: approximately 1.0 cm on average. Diameter: approximately 1.0 mm on average. Texture: smooth. Strength: strong. Aspect: erect. Color: commonly near Green Group 138B.

*Pedicels*.—Strength: strong. Aspect: erect. Length: approximately 5.0 mm on average. Diameter: approximately 1.0 mm on average. Texture: glabrous. Color: commonly near Greyed-Orange Group 177B.

*Reproductive organs*.—Androecium: Stamen: commonly 15 per flower, length is approximately 5.0 mm. Filament: length is approximately 5.0 mm, color is commonly near Red-Purple Group 63B. Anther: shape is globose, length is less than 1.0 mm on average, and color is commonly near Brown Group 200A. Pollen: amount is slight and coloration is commonly near White Group N155A. Gynoecium: syncarpous gynoecium with 5 styles fused to 1 ovary. Pistil: length is approximately 2.0 mm on average. Stigma: shape is fan shaped, and color is commonly near Red-Purple Group 63B. Style: length is approximately 1.5 mm on average and coloration is commonly near Red-Purple Group 62B. Ovary: length is approximately 0.5 mm on average and coloration is commonly near Yellow-Green Group 153C. Seed and fruit: none have been observed to date.

Development:

*Flowering season*.—Flowering in summer through early fall.

*Lastingness of individual inflorescence on the plant*.—Approximately 20 to 25 days on average.

*Tolerance to disease and pest*.—Not observed to date.

*Hardiness zone*.—USDA zone 5.

The new 'Iceconspir' variety has not been observed under all possible environmental conditions to date. Accordingly, it is possible that the phenotypic expression may vary somewhat with changes in light intensity and duration, cultural practices, and other environmental conditions.

I claim:

1. A new and distinct cultivar of *Spiraea* plant named 'ICECONSPIR', characterized by the following combination of characteristics:

(a) forms pink colored flowers, (b) displays blue-green colored foliage with burgundy colored new growth, and (d) forms a compact, mounding growth habit;

substantially as herein shown and described.

* * * * *